United States Patent [19]

Gait

[11] 4,079,079

[45] Mar. 14, 1978

[54] PROCESS FOR THE MONOACYLATION OF AN AROMATIC PRIMARY DIAMINE

[75] Inventor: Richard James Gait, Manchester, England

[73] Assignee: Imperial Chemical Industries Limited, London, England

[21] Appl. No.: 743,334

[22] Filed: Nov. 19, 1976

[30] Foreign Application Priority Data

Dec. 10, 1975 United Kingdom ............... 50642/75

[51] Int. Cl.$^2$ .......................................... C07C 102/00
[52] U.S. Cl. ............................................... 260/562 R
[58] Field of Search .................................... 260/562 R

[56] References Cited

U.S. PATENT DOCUMENTS

| | | | |
|---|---|---|---|
| 3,236,891 | 2/1966 | Seemuller | 260/562 R |
| 3,281,467 | 10/1966 | Wilson et al. | 260/562 R |
| 3,852,058 | 12/1974 | Huffman | 260/562 R |
| 3,919,269 | 11/1975 | Jaffe et al. | 260/562 R |
| 3,919,314 | 11/1975 | Marriott | 260/562 R |

OTHER PUBLICATIONS

Scott, Standard Methods of Chemical Analysis, D. Van Nostrand, N.Y., N.Y., 5th ed. 1946, vol. 2 pp. 2278–2281.

Roeder et al., J. Org. Chem. 6 (1940) pp. 25–29.

Primary Examiner—Arthur P. Demers
Attorney, Agent, or Firm—Cushman, Darby & Cushman

[57] ABSTRACT

A process for the monoacylating of an aromatic primary diamine containing no anionic water-solubilizing group, preferably m-phenylene or p-phenylenediamine, which comprises reacting an acylating agent in aqueous medium with a mineral acid salt, preferably the hydrochloric acid salt, of the diamine wherein the reaction mixture is maintained at a pH of from 1.5 to 3.5 during the addition and reaction of the acylating agent.

6 Claims, No Drawings

PROCESS FOR THE MONOACYLATION OF AN AROMATIC PRIMARY DIAMINE

This invention relates to a chemical process and more particularly to a process for the monoacylation of aromatic diamines.

Monoacylated derivatives of aromatic primary diamines are known compounds but are manufactured by somewhat inconvenient methods except where the presence of sulphonic acid groups produces suitable steric effects. Thus, m-aminoacetanilide has long been made by the acetylation of m-nitroaniline followed by reduction and p-aminoacetanilide by the nitration of acetanilide followed by reduction. However, in each case there are potential economies to be made if the corresponding diamine can be monoacylated without undue formation of the diacyl derivative.

It has been proposed in our OLS No. 2455212 to monoacylate aromatic primary diamines containing no sulphonic acid groups by the direct acylation of a mineral acid salt of the diamine. This document discloses that a maximum yield is obtained by the use of 2 – 2.5 equivalents of acid, and describes under such conditions the use of from 1.25 to more than 2 moles of acetic or propionic anhydride to form the mono-acyl derivative. Under such conditions, the pH of the reaction mixture remains below 1.

It has now been found that by carrying out the acylation at a higher pH, the amount of acylating agent used can be lowered to practically one mole/mole of diamine, thus effecting further economies in the cost of manufacture.

According to the present invention, there is provided a process for the monoacylation of an aromatic primary diamine containing no anionic water-solubilising group which comprises reacting an acylating agent in aqueous medium with a mineral acid salt of the diamine wherein the reaction mixture is maintained at a pH of from 1.5 to 3.5 during the addition and reaction of the acylating agent.

Diamines which may be acylated by the process of the invention contain no anionic water-solubilising groups but other substituents may be present on the aromatic nucleus, for example alkyl groups and halogen atoms. The process may be applied, e.g. to aromatic diamines of the benzene or naphthalene series, which in the former case may contain up to 2 substituents selected from alkyl or alkoxy of $C_{1-4}$ or chlorine, for example, 1,3-phenylenediamine
1,4-phenylenediamine
2,4-tolylenediamine
2,4-diaminoanisole
2,4-diaminochlorobenzene
2,5-diaminoanisole
1,2-phenylenediamine
2,6-tolylenediamine
1,4-diaminonaphthalene
1,5-diaminonaphthalene The new process is particularly suitable for the acylation of m-phenylene diamine and p-phenylene diamine.

Acylating agents which may be used in the process of the invention include acid chlorides and anhydrides of aromatic or aliphatic carboxylic acids, e.g. acetic anhydride, propionic anhydride and benzoyl chloride. In order to obtain a high yield of monoacylated derivative the acylating agent should be used in an amount of at least one mole per mole of diamine, but the need to use substantial excesses of anhydride is avoided by the new process and excellent yields can be obtained by using only 1.05 moles of acylating agent per mole of diamine.

The preferred mineral acid salt used in the process of the invention is the hydrochloride.

The new process can be carried out by forming a solution of the diamine, preferably of 15-20% by weight concentration, in aqueous mineral acid. Whilst the invention broadly contemplates the use of from 1.5 to just under 2 equivalents of mineral acid per mole of diamine in the original mixture, the preferred usage is from 1.7 to 1.8 equivalents of mineral acid per mole of diamine.

On adding the acylating agent to such a mixture it is found that the pH tends to drop, presumably because of the acid liberated during acylation. It is therefore necessary to add an acid-binding agent to neutralise the acid formed and maintain the pH of the mixture in the range of 1.5-3.5.

Many acid-binding agents can be used for this purpose; obviously ammonia or aliphatic amines which would themselves be liable to react with the acylating agent should not be used, but aliphatic tertiary amines, or more especially caustic alkalies, or alkali metal carbonates or bicarbonates should be suitable. The preferred acid-binding agent is caustic soda.

The temperature of the reaction mixture is preferably held within the range 0°-30° C, and more especially at 10°-15° C.

The product of the reaction may be isolated in conventional manner, for example by salting out the monoacylated diamine mineral acid salt.

The invention is illustrated but not limited by the following Examples in which all parts and percentages are by weight.

EXAMPLE 1

108 Parts of 1,4-phenylene diamine are added to an agitated mixture of 235 parts 28% hydrochloric acid and 330 parts water and cooled to below 15° C. 107 Parts of acetic anhydride are added to the above mixture over 4 hours, keeping the temperature below 15° C by cooling, and the pH between 1.5 and 3.5 by addition of 40% caustic soda solution. The reaction mixture is then stirred for 1 hour at 10°-15° C, then aqueous hydrochloric acid is added to bring the pH to 1 and 200 parts of salt are added. The 4-aminoacetanilide hydrochloride is isolated in 86% theory yield by filtration, and washing with 20% brine. It contains less than 1% diamine and 4% diacetyl derivative.

EXAMPLE 2

In place of the 1,4-phenylenediamine (108 parts) used in Example 1 there is used 1,3-phenylenediamine (108 parts). 3-Aminoacetanilide is obtained in 88.5% theory yield. It contains less than 1% diamine and 4% diacetyl.

EXAMPLE 3

In place of the 1,4-phenylenediamine (108 parts) used in Example 1 there is used 2,4-tolylenediamine (122 parts). 4-Acetylamino-2-toluidine is obtained in 78% theory yield. It contains less than 1% diamine and 4% diacetyl.

EXAMPLE 4

In place of the 1,4-phenylenediamine (108 parts) used in Example 1 there is used an 80:20 mixture of 2,4/2,6-tolylenediamine (122 parts). 4-Acetylamino-2-toluidine is obtained in 60% yield and contains less than 1% diamine and 4% diacetyl. None of the 6-isomer is isolated as this is much more soluble than the 4-derivative and is removed during the isolation and washing in the liquors.

EXAMPLE 5

138 parts of 2,4-diaminoanisole (1 mole) are added to an agitated mixture of 205 parts of 36% hydrochloric acid (2 moles) and 800 parts of water and cooled to below 10° C. 250 parts of acetic anhydride (2.45 moles) are added over 4-6 hours keeping the temperature at 0°–10° C by cooling and the pH at 1.5–3.5 by addition of 40% aqueous caustic soda solution. The mixture is then stirred for 1 hour and salt is added to precipitate the hydrochloride which is collected by filtration.

The yield is 80% of theoretical for the monoacylated diamine which is a mixture of the two possible isomers.

EXAMPLE 6

142.5 parts of 1-chloro-2,4-diaminobenzene (1 mole) are added to an agitated mixture of 205 parts of 36% hydrochloric acid (2 moles) and 800 parts of water and cooled to below 15° C. 200 parts of acetic anhydride (1.96 moles) are added over 4-6 hours keeping the temperature at 5°–15° C by cooling and the pH at 1.5–3.5 by addition of 40% aqueous caustic soda solution. The mixture is then stirred for 1 hour and salt is added to precipitate the hydrochloride which is collected by filtration.

The isolated yield is 69% of theoretical for the monoacylated diamine which is a mixture of isomers.

What we claim is:

1. A process for the monoacylation of an aromatic primary diamine containing no anionic water-solubilising group which comprises reacting an acylating agent in aqueous medium with a mineral acid salt of the diamine wherein the reaction mixture is maintained at a pH of from 1.5 to 3.5 during the addition and reaction of the acylating agent.

2. A process as claimed in claim 1 wherein the aromatic primary diamine is m-phenylenediamine or p-phenylenediamine.

3. A process as claimed in claim 1 or wherein the mineral acid salt used is the hydrochloric acid salt.

4. A process as claimed in claim 2 wherein the amount of acylating agent is one mole per mole of diamine.

5. A process as claimed in claim 4 wherein caustic soda is added to the reaction mixture to maintain the pH in the range of 1.5–3.5.

6. A process as claimed in claim 4 wherein the diamine is m-phenylenediamine or p-phenylenediamine; the mineral acid salt is the hydrochloric acid salt, the acylating agent is acetic anhydride and the reaction temperature is kept between 0° and 30° C.

* * * * *